United States Patent [19]

Aoki et al.

[11] Patent Number: 4,707,147
[45] Date of Patent: Nov. 17, 1987

[54] DEVICE FOR MEASURING PLASMA PROPERTIES

[75] Inventors: Yoshiaki Aoki; Naoyuki Kayukawa; Hatsuo Yamazaki; Yasutomo Ozawa; Hiroki Kitagawa, all of Sapporo, Japan

[73] Assignee: Hokkaido University, Sapporo, Japan

[21] Appl. No.: 815,071

[22] Filed: Dec. 30, 1985

[30] Foreign Application Priority Data

Feb. 19, 1985 [JP] Japan .................................. 60-29407

[51] Int. Cl.⁴ .......................... G01J 5/58; G01N 21/21
[52] U.S. Cl. ...................................... 374/161; 356/43; 356/73
[58] Field of Search ........................ 374/159, 161, 126; 356/43, 364, 73

[56] References Cited

U.S. PATENT DOCUMENTS

| | | | |
|---|---|---|---|
| 3,317,737 | 5/1967 | Kopsel et al. | 356/43 X |
| 3,462,224 | 8/1969 | Woods et al. | 356/43 X |
| 3,734,620 | 5/1973 | Cade | 356/73 |
| 3,817,622 | 6/1974 | Billman et al. | 356/43 X |
| 4,020,695 | 5/1977 | Roney | 374/126 X |
| 4,140,393 | 2/1979 | Cetas | 374/161 |
| 4,498,765 | 2/1985 | Herve | 356/43 |

OTHER PUBLICATIONS

"Spectroscopic Gas Temperature Measurement" by Richard H. Tourin, Elsevier Publishing Company, 1966, pp. 24–40.

"The Direct Measurement of Electron Density in an MHD Duct" by J. D. E. Beynon et al., Warsaw Symposium, Jul. 24–30, 1968, pp. 28–31 (vol. I).

Primary Examiner—Daniel M. Yasich
Attorney, Agent, or Firm—Spencer & Frank

[57] ABSTRACT

A device for measuring properties of plasma projects linearly polarized light to an object plasma as incident light, and the light coming from the plasma in response to the incident light is separated into an S-polarized component and a P-polarized component, so that temperature and other properties of the plasma are determined from such S- and P-polarized components.

15 Claims, 7 Drawing Figures

DEVICE FOR MEASURING PLASMA PROPERTIES

BACKGROUND OF THE INVENTION

1. Field of the Invention

This invention relates to a device for optically measuring plasma properties.

2. Related Art Statement

MHD power generation, that is, power generation by the use of magnetohydrodynamics, as a new technology for generating electricity, has the great advantage of directly converting the energy of a high-temperature fluid into electrical energy by flowing high-temperature fuel gas plasma in a direction perpendicular to a magnetic field. The electromotive forces of the MHD power generation are induced by the Faraday effect in two directions, i.e., in a direction perpendicular to the magnetic field and in a direction perpendicular to the plasma flow. It is necessary in MHD power generation to maintain the high-temperature plasma under desired conditions. To this end, there is a strong demand for developing a device which accurately measures the temperature, electron density, conductivity and other physical properties of the plasma.

There is a conventional method for optically measuring plasma temperature based on the so-called line reversal principle. According to the line reversal principle, a reference light source projects light flux of various light source temperatures onto a plasma, and one detects that light source temperature at which the light flux incident on the plasma is not absorbed by the plasma and plasma emission does not cause any increase of light intensity. Such light source temperature is treated as being equal to the plasma temperature, whereby the plasma temperature is detected. Methods based on the line reversal principle can measure a plasma temperature of up to about 3,000° K., and such methods include a wavelength sweeping method, a matching method, a chopper method, and a knife edge method.

Figure 5:
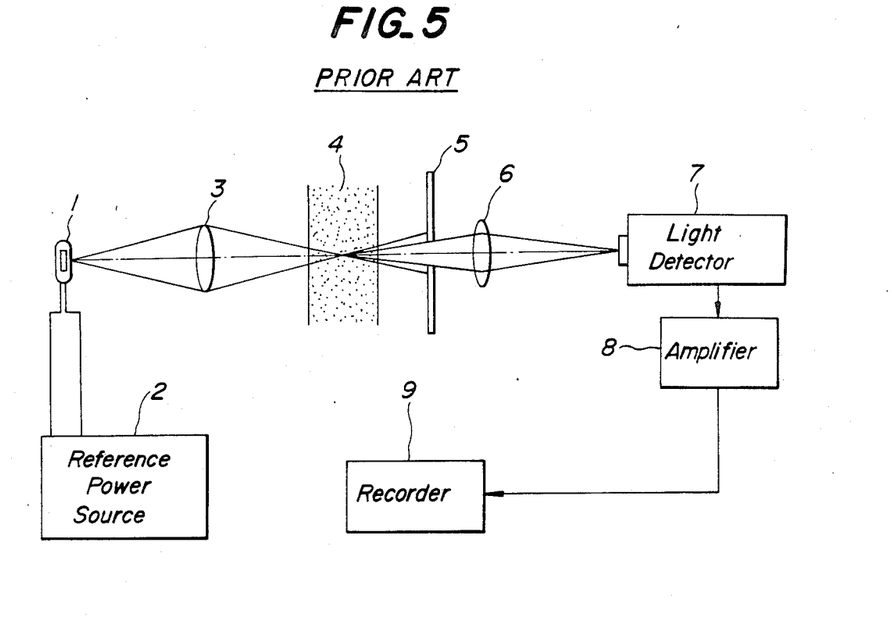
FIG. 5 is a schematic diagram of a conventional device for measuring plasma temperature based on a wavelength sweeping method.
Figure 6:
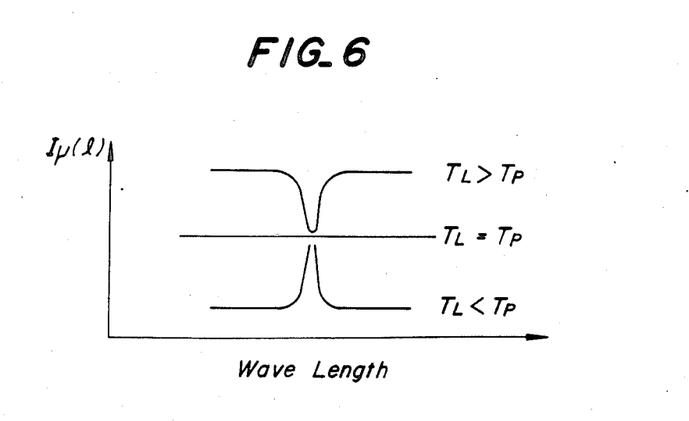
FIG. 6 is a graph showing the spectrographic properties of light fluxes from different light source temperatures.

FIG. 5 shows a schematic diagram of a device for measuring the plasma temperature by the wavelength sweeping method. A light source 1 of white light is connected to a reference power source 2, and light fluxes of various light source temperatures are radiated from the light source 1 by changing the output from the reference power source 2 and such light fluxes are projected onto a plasma 4 through a condenser lens 3. The light fluxes which have passed the plasma 4 become incident on a spectrophotometer 7 through a slit 5 and another condenser lens 6, and the spectrographic property of such light fluxes through the plasma 4 are detected. The detected spectrographic properties are stored in a recorder 9 through an amplifier 8. Depending on the light source temperature $T_L$ at the light source 1, the light fluxes through the plasma 4 are affected by light emission or absorption in the plasma 4 in the resonant wavelength range as shown in FIG. 6. More particularly, when the light source temperature $T_L$ is below the plasma temperature $T_p$, the light intensity is increased by the light emission in the plasma in the proximity of the resonant wavelength, while when the light source temperature $T_L$ is above the plasma temperature $T_p$, light absorption is caused. When the light source temperature $T_L$ is equal to the plasma temperature $T_p$, neither light emission nor light absorption is caused. Accordingly, if the spectrographic light intensity characteristics of the light fluxes through the plasma 4 is measured while varying the light source temperature of the white light source 1, the plasma temperature $T_p$ can be determined.

Figure 7:
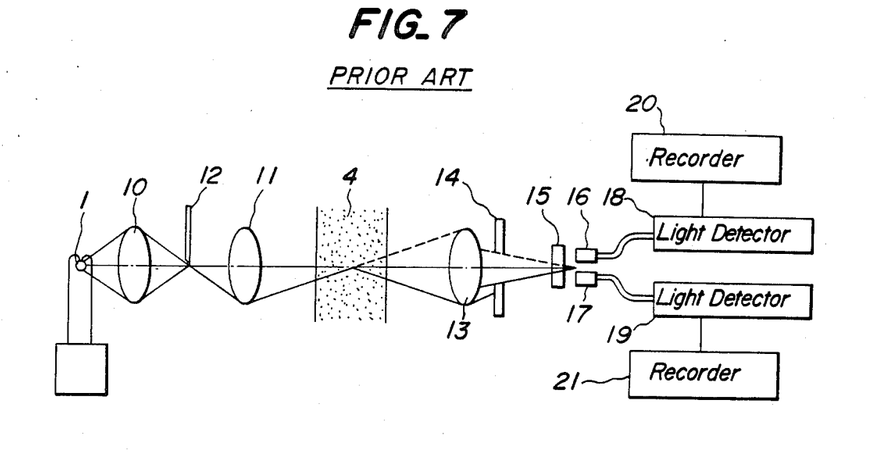
FIG. 7 is a schematic diagram of another conventional device for measuring plasma temperature which device is based on the knife edge method.

FIG. 7 shows a schematic diagram of a device for measuring the plasma temperature by the knife edge method. In the knife edge method, two condenser lenses 10 and 11 are disposed between the light source 1 and the plasma 4, and a knife 12 is disposed between the two condenser lenses 10 and 11. Whereby, due to the presence of the knife 12, only those light fluxes which pass below an optical axis shown on the figure are allowed to become incident on the plasma 4. The light fluxes which leave the plasma 4 pass through a condenser lens 13, a slit 14 and a filter 15, and enter into light guides 16 and 17, which light guides are disposed above and below the optical axis. Light detectors 18 and 19 are disposed on the output sides of the light guides 16 and 17, and the outputs from the light detectors 18 and 19 are stored in recorders 20 and 21 respectively. Those light fluxes from the light source 1 which come into the space above the optical axis are interrupted by the knife 12, so that the light detector 16 located above the optical axis detects only the light fluxes radiated by the plasma radiation field, while the light detector 17 located below the optical axis detects the sum of the flux from the light source 1 and the fluxes radiated from the plasma radiation field. Thus, the plasma temperature $T_p$ is measured based on the output signals from the light detectors 16 and 17.

The above-mentioned wavelength sweeping method has a shortcoming in that, since the light source temperature of the white light source is required to be successively changed in order to allow the measurement of the spectrographic properties at each light source temperature, it takes a long time to complete the measurement, and the conditions of the plasma are changed during the measurement, so that the plasma temperature of one spatial point at a specific time can not be determined. It has another shortcoming in that the plasma temperature can be measured only at discrete points, and continuous measurement with respect to time is impossible. Further, theoretically speaking, only the approximate temperature is measured and the reliability of the measured value is not very high.

The knife edge method also has a shortcoming in that there is no spatial coincidence between the light fluxes coming from the light source through the plasma and the light fluxes radiated from the plasma radiation field, so that a serious measurement error may be caused when there is any significant localized variation of plasma conditions.

The above shortcomings are noticed not only in the plasma measurement but also in other measurement of quickly varying physical phenomenon such a nuclear fusion reaction and an electric discharge.

SUMMARY OF THE INVENTION

Therefore, an object of the invention is to obviate the above-mentioned shortcomings of the prior art by providing a novel device for measuring plasma properties, which device can measure the plasma properties of one spatial point at a specific time and also can measure them continuously with respect to time.

A preferred embodiment of the device for measuring plasma properties of the invention comprises a light source projecting linearly polarized light to a plasma as an incident light, a means for separating light coming from the plasma in response to the incident light into an S-polarized component and a P-polarized component, and a means for detecting the S-polarized component and the P-polarized component respectively so as to determine the temperature of the plasma based on the detected values of both the S-polarized component and the P-polarized component.

Another embodiment of the device for measuring plasma properties in accordance with the invention comprises a first light source and a second light source which light sources project linearly polarized light beams of different wavelengths onto a plasma along a common optical axis, a means for dividing light fluxes coming from a plasma into two light flux portions, a means for separating one of the two divided light flux portions into an S-polarized component and a P-polarized component, a means for detecting the S-polarized and the P-polarized components respectively, and a means for detecting the Faraday rotation angle of the other one of the two divided light flux portions.

In the device of the invention, linearly polarized light is projected onto a plasma, and a combination of light flux coming from the light source through the plasma and the light flux radiated from that portion of the plasma radiation field which lies on the passage of the light flux from the light source is received. The S-polarized component and the P-polarized component in the received combination of light fluxes are separated, and the separated S- and P-polarized components are detected by light detectors. The outputs from the light detectors are applied to an operational processor device, so that the plasma properties are continuously measured with respect to time.

In another embodiment of the invention, both linearly polarized light of short wavelength which is hardly effected by the Faraday effect due to the magnetic field generated by the plasma and linearly polarized light of long wavelength which is easily affected by the Faraday effect are projected to a plasma along a common optical axis. The light fluxes leaving the plasma are divided into two portions, and the desired plasma temperature is detected by finding out the S-polarized component and the P-polarized component of one of the two portions of the light fluxes, while other physical properties such as electron density and electric conductivity are measured by finding out the Faraday rotation angle of the other one of the two portions due to the magnetic field generated by the plasma. Thus, various plasma properties at a specific spatial point can be simultaneously measured.

BRIEF DESCRIPTION OF THE DRAWINGS

For a better understanding of the invention, reference is made to the accompanying drawings, in which.

Throughout the different views of the drawings, 1 is a light source of white light, 2 is a reference power source, 3, 6, 10, 11, 13, 34 and 37 are condenser lenses, 4 and 35 are plasmas, 5, 14, 36, 39 and 53 are slits, 7 is a spectrophotometer, 8, 44, 48, 59 and 60 are amplifiers, 9, 20 and 21 are recorders, 12 is a knife, 15, 42 and 46 are filters, 16 and 17 are light guides, 18 and 19 are light detectors, 30 is a light source, 31 is a reference power source, 32 and 40 are collimator lenses, 33 is a polarizer, 38 is a detector unit, 41 is a beam splitter, 43 is a first light detector, 45 and 61 are operational processor devices, 47 is a second light detector, 50 is a second light source, 51, 52 and 54 are half mirrors, 55 and 57 are analyzers, 56 is a third light detector and 58 is a fourth light detector.

DESCRIPTION OF THE PREFERRED EMBODIMENTS

Figure 1:
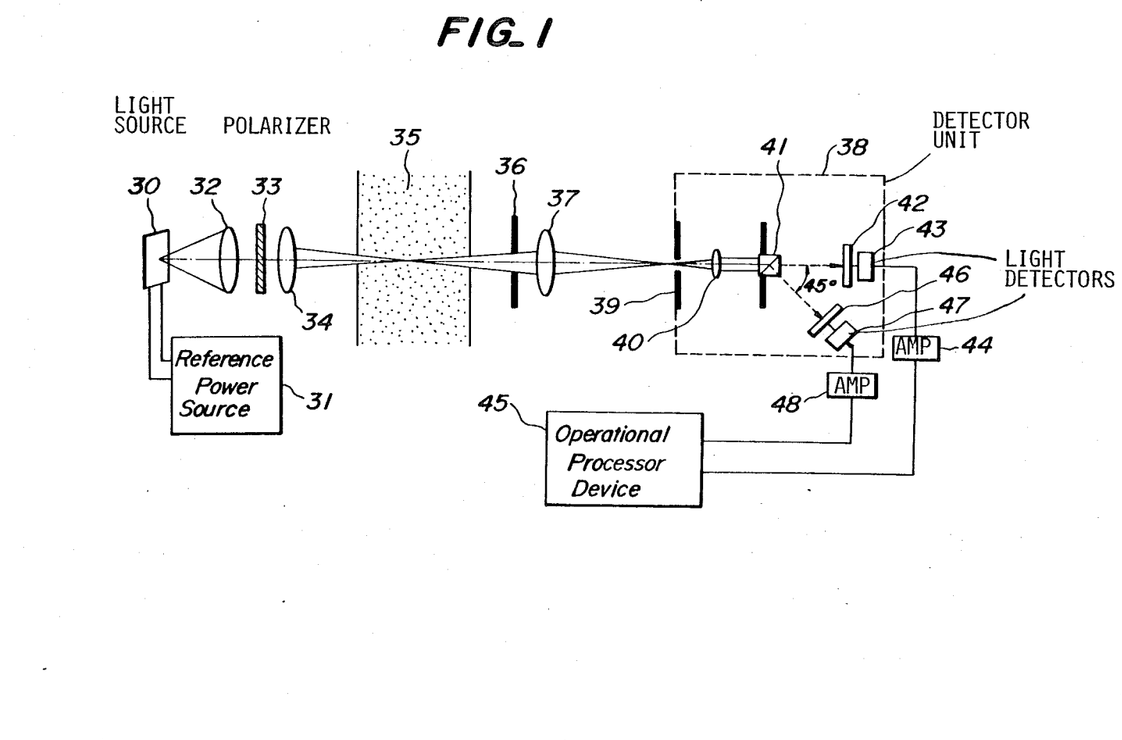
FIG. 1 is a schematic diagram showing a device for measuring plasma properties according to the invention.

FIG. 1 is a schematic diagram of a device for measuring plasma properties according to the invention. The illustrated example is to measure the plasma temperature. A light source 30 is connected to a reference power source 31, so that light flux with a desired brightness is emanated from the light source 30. The light flux from the light source 30 is made into parallel light flux by a collimator lens 32, and linearly polarized light consisting of an S-polarized component or a P-polarized component is produced by passing the parallel light flux through a polarizer 33. In this example, linearly polarized light with the S-polarized component is to be passed, and the linearly polarized light with the S-polarized component is condensed by a condenser lens and projected onto a plasma 35.

The light flux projected onto the plasma 35 is condensed in the plasma 35, and then emanated from the plasma 35. The emanated light flux passes through a slit 36 and condensed by a condenser lens 37 and enters into a detector unit 38. The incident light flux onto the detector unit 38 from the plasma 35 includes the light flux coming from the light source 30 through the plasma 35 and light flux radiated from that plasma radiation field which lies on the passage of the light flux in the plasma 35. The plasma radiation field is optically isotropic, so that the S-polarized components and P-polarized components are equally radiated. Accordingly, the detector unit 38 receives both such S-polarized component from the light source 30 through the plasma 35 and such S-polarized component radiated from the plasma radiation field. As to the P-polarized component, the detector unit 38 receives only the P-polarized component radiated from the plasma radiation field.

The incident light flux to the detector unit 38 passes through a slit 39 and is made into parallel light flux by a collimator lens 40 and enters into a beam splitter 41. The beam splitter 41 of this example is a Gran Thomson prism, and this Gran Thomson prism separates the incident light flux thereto into an S-polarized component and a P-polarized component. The S-polarized component thus separated passes through a filter 42, and a component of a certain wavelength thereof enters into a first light detector 43 so as to be converted into an electric signal. The electric signal from the first light detector 43 enters into an operational processor device 45 through an amplifier 44. On the other hand, the P-polarized component proceeds towards another filter 46 along an optical path which is deviated from the optical path of the S-polarized component by 45°, and a second light detector 47 receives such P-polarized component and converts it into an electrical signal. The electrical signal from the second light detector 47 also enters the operational processor device 45 through another amplifier 48.

The method of analysis will be explained now.

Figure 2:
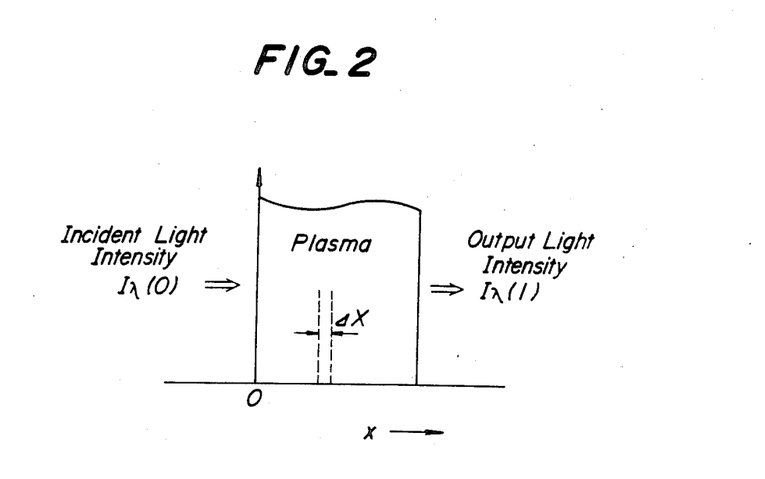
FIG. 2 is a diagrammatic illustration of the principle of the optical measurement of plasma temperature.

FIG. 2 shows a diagrammatic illustration of the principle of the optical measurement of plasma temperature. It is assumed that the observation hole of the plasma radiation field is sufficiently small as compared with the magnitude of the plasma, so that the plasma radiation field can be treated by a one-dimensional approach. If local thermal equilibrium is assumed, the following equation can be obtained.

$$\frac{dI_\lambda(x)}{dx} = \epsilon_p(\lambda, T_p) - k_p(\lambda, T_p) I_\lambda(x) \qquad (1)$$

here,
$T_p$: plasma temperature
$\epsilon_p$: emissivity of the plasma
$k_p$: absorption coefficient of the plasma.

If the plasma is homogeneous, equation (1) can be modified by using the light intensity l as follows:

$$I_\lambda(l) = I_\lambda(o)e^{-k\lambda l} + \frac{\epsilon_p(\lambda)}{k_p(\lambda)}\{1 - e^{-k\lambda l}\} \qquad (2)$$

here, $k_\lambda$: corrective factor for absorption by the optical system. Due to Kirchhoff's law, $$\frac{\epsilon_p(\lambda)}{k_p(\lambda)} = B_\lambda(Te) \qquad (3)$$

here,
Te: electron temperature of the plasma, and
$B_\lambda$: intensity of light emission from the plasma.

If the brightness temperature of the light source is designated by $T_L$ and if a light source calibrated for the brightness temperature is used, the incident light $I_\lambda(o)$ is given by the following equation (4).

$$I_\lambda(o) = B_\lambda(T_L) \qquad (4)$$

If the wavelength range of the measurement taken is in that of visible light, the Wien approximation can be applied and one can get the following equation.

$$B(T) = C_1 \lambda^{-5} \cdot e^{-\frac{C_2}{\lambda T}} \qquad (5)$$

$C_1 = 1.191 \times 10^{-5}$ erg · cm²/sec, and $C_2 = 1.438$ cm · K

Accordingly, the equation (2) can be simplified as follows by using the brightness temperature $T_L$ of the light source, the electron temperature Te of the plasma and the intensity l of the light source.

$$I_\lambda(l) = B(T_L) \cdot e^{-k\lambda l} + B_\lambda(Te)\{1 - e^{-k\lambda l}\} \qquad (6)$$

Since it is assumed that only the S-polarized component obtained from the natural light of the light source 30 by the polarizer 33 is projected onto the plasma 35, the incident light intensity $\phi'_{LS}$ of the incident S-polarized component to the plasma 35 from the light source 30 can be given by $$\phi'_{LS} = \xi \cdot \iota \cdot \phi_L = \xi \cdot \iota \cdot K_1 \cdot B_\lambda(T_L) \qquad (7)$$

here,
$\phi_L$: intensity of light flux emanated from the light source
$\eta$: conversion efficiency of the polarizer
$\xi$: transmission coefficient of the polarizer for the linearly polarized light
$K_1$: correction factor for the optical system from the light source to the plasma.

The intensity $\phi_{LS}$ of the incident light flux to the light detector 43 from the light source 30 after passing through the plasma 35 can be given by $$\phi_{LS} = \xi^2 \cdot \eta \cdot K_1 \cdot K_2 \cdot B_\lambda(T_L) \cdot e^{-k\lambda \cdot l} \qquad (8)$$

here, $K_2$: correction factor for the optical system from the plasma to the light detector. On the other hand, since the light radiated from the plasma 35 is optically isotropic, the S-polarized component and the P-polarized component of the linearly polarized light radiated therefrom are substantially the same. Thus, the S-polarized component $\phi_{PS}$ and P-polarized component $\phi_{pp}$ of the linearly polarized light radiated from the plasma radiation field and detected by the light detectors 43 and 47 are given by the following equation.

$$\phi_{PS} = \phi_{PP} = \xi \cdot \eta \cdot K_2 \cdot B_\lambda(Te)\{1 - e^{-k\lambda \cdot l}\} \qquad (9)$$

The S-polarized component received by the first light detector 43 is the sum of the S-polarized component of the linearly polarized light from the light source 30 through the plasma 35 and the S-polarized component of the linearly polarized light radiated from the plasma field. Accordingly, the intensity $\phi_S$ of the incident light to the first light detector 43 is given by the following equation.

$$\phi_S = \phi_{LS} + \phi_{PS} \qquad (10)$$

On the other hand, the second light detector 47 receives the P-polarized component which is only that of the linearly polarized light radiated from the plasma radiation field. Accordingly, the intensity $\phi_p$ of the incident light to the second light detector 47 is given by the following equation:

$$\phi_P = \phi_{PP} \qquad (11)$$

Hence, the electron temperature Te of the plasma is given by $$Te = T_L \left\{ 1 - \frac{\lambda \cdot T_L}{C_2} \ln \left[ \frac{\xi \cdot K_1 \cdot \phi_{PP}}{\phi_{LS} - \phi_S + \phi_P} \right] \right\}^{-1} \qquad (12)$$

The equation (12) shows that the electron temperature Te of the plasma can be measured by separately detecting the intensity $\phi_{LS}$ of the incident light to the plasma 35, and intensity $\phi_S$ of the S-polarized incident light to the first light detector 43, and the intensity $\phi_p$ of the P-polarized incident light to the second light detector 47. If the plasma 35 is in thermal equilibrium, the plasma temperature Tp is equal to electron temperature Te of the plasma, and the plasma temperature Tp can be measured. If the equation (12) is stored in an operational processor device 45 which is connected to both the first light detector 43 and the second light detector 47, the output from the first light detector 43 and the second light detector 47 are continuously processed by the operational processor device 45 so that the temperature of the plasma 35 can be continuously measured with respect to time.

Figure 3:
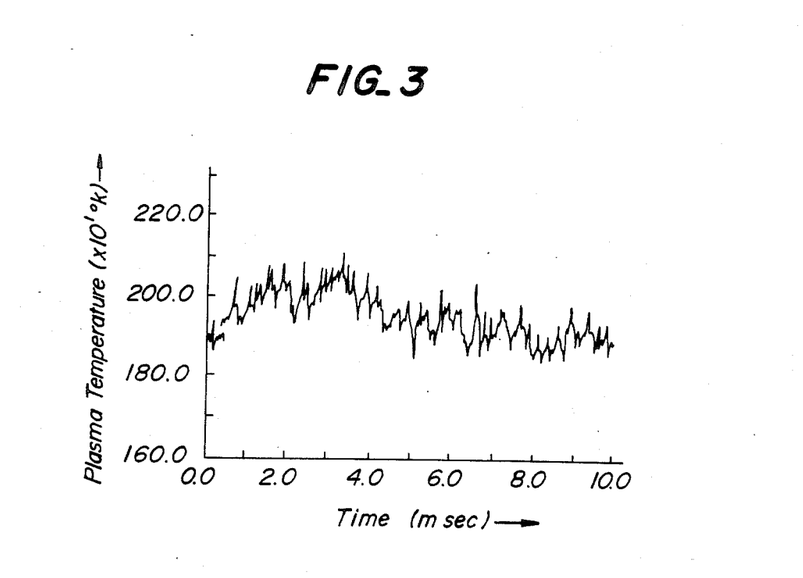
FIG. 3 is a graph showing an example of the plasma temperature variations measured by the device of the invention.

FIG. 3 shows a graph of an example of the plasma temperature measurement which was made by using the device described above. In the figure abscissa represents time, while the ordinate represents the plasma temperature. It can be seen from the FIG. 3 that, with the device for measuring plasma properties according to the invention, the plasma temperature can be measured at high speed with a time resolution in the order of 2 microseconds. The illustrated example of the measured results shows that the local temperature of the plasma varies at a high speed due to localized Joule heating caused by electric currents in the plasma.

Figure 4:
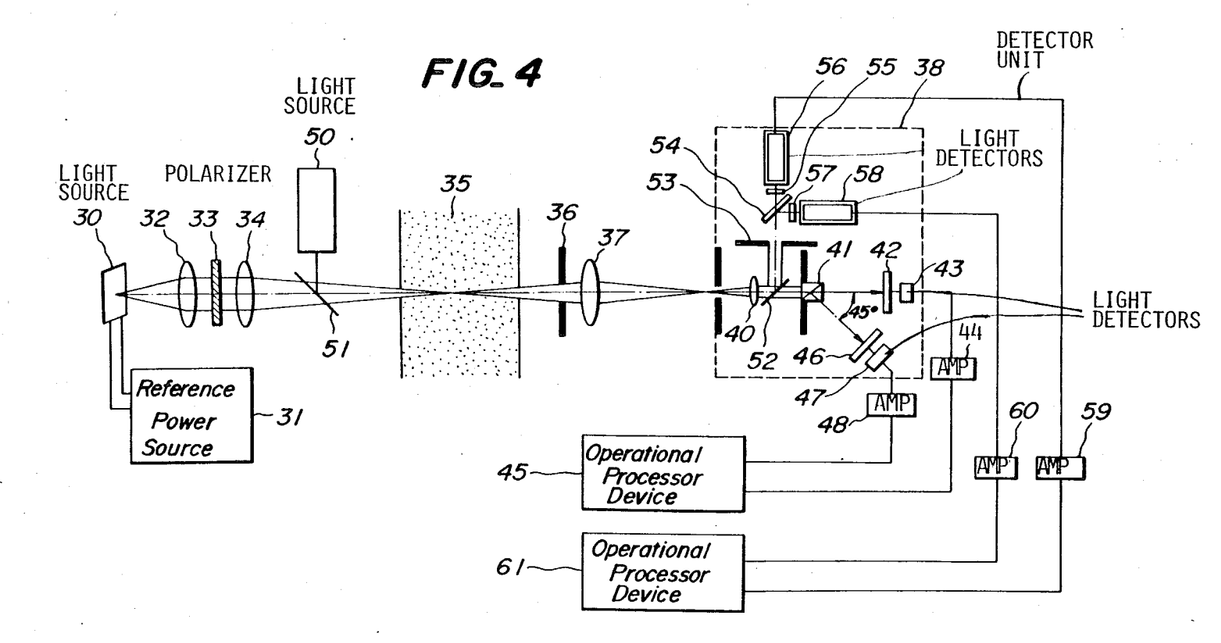
FIG. 4 is a schematic diagram of an embodiment of the device for measuring plasma properties which embodiment uses two kinds of light sources.

FIG. 4 is a schematic diagram showing another embodiment of the device for measuring plasma properties according to the invention, which embodiment simultaneously measures the conductivity and electron density of a plasma together with the plasma temperature. In the figure, like parts of those of the FIG. 1 are shown by like numerals. In this embodiment, various physical properties of the plasma such as the electron density thereof is measured by detecting the Faraday rotation angle, at the same time as the plasma temperature measurement is made in the above-mentioned manner. The wavelength range in which the Faraday effect due to the magnetic field formed by the plasma is caused lies in a fairly long wavelength range. In this embodiment of the present invention, the first light source 30 emanates linearly polarized light of comparatively short wavelength which is hardly susceptible to the Faraday effect so as to measure the plasma temperature. To measure other properties of the plasma, a second light source 50 is provided, which light source 50 emanates linearly polarized light of longer wavelength than that from the first light source 30, the longer wavelength light being more susceptible to the Faraday effect. A preferable example of the second light source 50 is for instance a semi-conductor laser emanating far infrared rays in the order of 15,000 Å.

The light flux emanated from the second light source 50 is reflected by a half mirror 51 whose optical axis is in coincidence with that of the above-mentioned optical system of the first embodiment. The reflected light flux from the half mirror 51 is projected onto the plasma 35 together with the light flux emanated from the light source 30. The light flux leaving the plasma 35 enters into the detector unit 38 through the slit 36 and the condenser lens 37. The light flux entering the detector unit 38 is converted into parallel flux by the collimator lens 40 and then becomes incident on a half mirror 52. The light flux passing through the half mirror 52 enters into the beam splitter 41, while the light reflected by the half mirror 52 passes through a slit 53 and becomes incident on another half mirror 54. There are two wavelengths in the light fluxes entering the beam splitter 41 from the half mirror 52, and both the first light detector 43 and the second light detector 47 are made sensitive to short-wavelength light, such as the light from the light source 30, so that they are not affected by the light flux from the second light source 50. Accordingly, the second light source 50 may emanate either of the S-polarized component and the P-polarized component.

The light flux incident to the beam splitter 41 is separated into the S-polarized component and the P-polarized component by the above-mentioned optical system, and the operational processor device 45 processes the separated S-polarized component and P-polarized component for determining the plasma temperature Tp in the above explained manner. On the other hand, the light flux incident on the half mirror 54 is partly reflected by it, and the light flux passing therethrough becomes incident on a third light detector 56 through an analyzer 55. The light flux reflected by the half mirror 54 becomes incident on a fourth light detector 58 through another analyzer 57. The third light detector 56 and the fourth light detector 58 receive the light flux both from the first light source 30 and from the second light source 50, but the third light detector 56 and the fourth light detector 58 are made sensitive only to long-wavelength light fluxes so that only the light flux from the second light source 50 is detected thereby.

The third light detector 56 and the fourth light detector 58 are connected to another operational processor device 61 through amplifiers 59 and 60 respectively. The plane of polarization of the long-wavelength light flux emanated from the second light source 50 is rotated by the magnetic field generated by the plasma 35 while such light flux passes through the plasma 35. The Faraday rotation angle $\theta$ of such rotation is detected by operating the analyzer 57. As the amount of the plasma 35 varies, the Faraday angle $\theta$ also fluctuates. If the relationship between the amount of plasma and the output from the light detector is stored in the operational processor device 61 beforehand, the Faraday angle $\theta$ detected as the output from the third light detector 56 can be corrected so as to eliminate the effect of the variation of the amount of plasma. Information relating to the variation of the amount of plasma can be determined by applying the outputs from the first light detector 43 and the second light detector 47 for plasma temperature measurement to the operational processor device 61, provided that a suitable program therefor is preloaded in the device 61.

The process for determining various plasma properties from the thus measured Faraday rotation angle $\theta$ will be explained now. The Faraday rotation angle $\theta$ produced during the passage of the linearly polarized light through the plasma is given by the following equation.

$$\theta = \frac{eBd}{2mc^2} \times \frac{\omega^2}{n} \times \frac{Ne^2}{m(\omega_0^2 - \omega^2)} \qquad (13)$$

here,
B: magnetic field intensity of the plasma
m: mass of an electron
$\omega$: frequency of the incident light
$\omega_o$: characteristic frequency of the plasma electron
n: refractive index of the plasma
N: electron density of the plasma
d: thickness of plasma
e: quantum of electricity c: light velocity.

In equation (13), the quantities B, M, $\omega$, n, d, e and c can be treated as known. Accordingly, if the characteristic frequency $\omega_o$ of the plasma electron is found, the electron density N of the plasma can be determined from the Faraday rotation angle $\theta$. Two Faraday rotation angles $\theta_1$ and $\theta_2$ of those two frequency components in the linearly polarized light are measured beforehand, which two frequency components have frequencies $\omega_1$ and $\omega_2$ much higher than the plasma frequency $\omega_p$, namely $\omega_1$, $\omega_2 >> \omega_p$. If notations of $\alpha = \omega_2/\omega_1$, $\beta = \theta_2/\theta_1$ are assumed, the characteristic frequency $\omega_o$ of the plasma electrons can be given by the following equation (14).

$$\omega_o^2 = \frac{\omega_1 \omega_2 \{\alpha(1-\beta) \pm \sqrt{\beta} (1-\alpha^2)\}}{(\alpha^2 - \beta^2)} \quad (14)$$

Accordingly, the electron density N of the plasma can be given by the following equation by using the thus determined characteristic frequency $\omega_o$.

$$N = \frac{\theta(\omega_o^2 - \omega^2)^2}{a\omega^2} \quad (15)$$

here, $$a = \frac{e^3 B d}{2m^2 nc}$$

Accordingly, the electron density N of the plasma can be easily calculated by the equation (15) while using the Faraday rotation angle $\theta$ which is measured by the operational processor device 61.

The conductivity $\sigma$ of the plasma will be determined next. The conductivity $\sigma$ is given by $$\sigma = Ne\sigma \quad (16)$$

here,
N: electron density of the plasma
e: quantum of electricity
$\mu$: mobility of electron in the plasma
The mobility $\mu$ of electron in the plasma can be determined beforehand by a separate method, so that it can be treated as known. Accordingly, the conductivity $\sigma$ of the plasma can be finally determined through the calculation of equation (16) based on the electron density N of the plasma as determined by the operational processor device 61.

The degree of electrolytic dissociation $\alpha$ and collision cross section Q can be determined. The conductivity $\sigma$ of the plasma can be expressed by the following equation which is derived from an equation representing the electric conductivity of a weakly dissociated gas.

$$\sigma = \frac{3.34 \times 10^{-12} \alpha}{QT^{\frac{1}{2}}} \quad (17)$$

here,
$\alpha$: degree of electrolytic dissociation
Q: collision cross section
T: plasma temperature
Thus, when the plasma temperature T is found by the above explained method, one of the degree of electrolytic dissociation $\alpha$ and the collision cross section Q of the plasma can be determined provided that either the collision cross section Q or the degree of dissociation $\alpha$ of the plasma is measured beforehand.

The invention is not restricted to the above embodiments and numerous changes and modifications are possible. For instance, although the light source for the measurement of plasma temperature in the above embodiment is a combination of a white light source and a polarizer, it is also possible to use other source of linearly polarized light such as a semiconductor laser. However, it should be noted that the light source temperature must be in a proper range. Further, the Gran Thomson prism used in the above embodiments as a beam splitter can be replaced with any other suitable polarizer prism such as the Nicol's prism.

The outstanding features of the invention can be summarized as follows:

(1) The plasma temperature is measured by projecting linearly polarized light onto a plasma and measuring both the linearly polarized light through the plasma and the light radiated from the plasma radiation field at the position where the projected light passes, so that the plasma temperature at a particular spatial point at a particular time can be determined. Thus, the reliability of the plasma temperature measurement can be improved. Besides, in contrast to the conventional approximate measurement of the plasma temperature, the device of the present invention directly determines the plasma temperature so that the measuring accuracy is much improved.

(2) The plasma temperature can be determined directly from the output of light detectors without measuring any spectrographic characteristics, so that the plasma temperature can be measured continuously with regard to time. Consequently, the device of the invention facilitates easy control of plasma at a high accuracy.

(3) Since two kinds of light flux with different wavelengths are applied onto a plasma from two light sources along a common optical axis, various physical properties of the plasma at a particular spatial point can be measured simultaneously.

What is claimed is:

1. Apparatus for optically measuring the electron density and conductivity of a plasma, comprising
   a source of linearly polarized light, said light being incident on said plasma;
   separation means for separating light emanating from said plasma into two components;
   detection means for detecting said two light components;
   analyzer means interposed between said separation means and said detection means for measuring the Faraday angle of said plasma; and
   processing means coupled to said detection means for measuring the electron density and conductivity of said plasma, said electron density and conductivity being determined, for plasma electrons having a predetermined characteristic frequency, from the Faraday rotation angle of said plasma as measured by said analyzer means.

2. Apparatus for optically measuring the electron density and conductivity of a plasma as set forth in claim 1, wherein the conductivity and electron density of said plasma are determined by solving in said processing means the equations $$N = \frac{\theta(\omega_0^2 - \omega^2)^2}{a\omega^2} \text{ and}$$

$$\sigma = Ne\mu, \text{ respectively,}$$

where N is the electron density of the plasma, $\theta$ the Faraday rotation angle of said plasma measured by said analyzer, $\omega_0$ the characteristic frequency of the plasma electrons, $\omega$ the frequency of the incident light, e a quantum of electricity, $\mu$ the mobility of electrons in the plasma and $$a = \frac{e^3 B d}{2m^2 nc}, \text{ where}$$

B is the magnetic field intensity of the plasma, d the thickness of the plasma, m the mass of an electron, n the refractive index of the plasma, and c the velocity of light.

3. Apparatus for optically measuring the temperature of a plasma, comprising
  a source of linearly polarized light, said linearly polarized light being incident on said plasma;
  separation means for separating light emanating from said plasma into an S-polarized component and a P-polarized component;
  detection means for detecting said S-polarized and P-polarized components, said detection means generating first and second output signals corresponding to said S-polarized and P-polarized components respectively, and
  processing means coupled to said detection means for measuring the electron temperature of said plasma, said electron temperature being determined, for a light source having a predetermined brightness temperature and wavelength, from the first and second output signals of said detection means.

4. Apparatus for optically measuring the temperature of a plasma as set forth in claim 3, wherein the electron temperature of said plasma is determined by solving in said processing means the equation $$Te = T_L \left\{ 1 - \frac{\lambda \cdot T_L}{C_2} \ln \left[ \frac{\xi \cdot K_1 \cdot \phi_P}{\phi_{LS} - \phi_S + \phi_P} \right] \right\}^{-1}$$

where, Te is the plasma electron temperature, $T_L$ the brightness temperature of the light source, $\lambda$ the wavelength of the light generated by the light source, $C_2$ a correction factor, $\xi$ the transmission coefficient of a polarizer for linearly polarizing the light, $K_1$ a correction factor for an optical system between the light source and the plasma, $\phi_p$ the output from the detection means for detecting the P-polarized component, $\phi_{LS}$ the intensity of the light flux after passing through the plasma, and $\phi_S$ the output from the detection means for detecting the S-polarized component.

5. Apparatus for optically measuring the electron temperature, electron density and conductivity of a plasma, comprising
  a first source of linearly polarized light having a first wavelength;
  a second source of linearly polarized light having a second wavelength different from said first wavelength, the linearly polarized light emitted by said first and second sources being incident on said plasma along a common optical axis;
  dividing means for dividing light emanating from said plasma in response to light from said first and second sources into first and second light portions;
  first separation means for separating the light in said first portion into an S-polarized component and a P-polarized component;
  first detection means for detecting said S-polarized and P-polarized components in said first portion and generating first and second output signals corresponding to said S-polarized and P-polarized components respectively;
  first processing means coupled to said first detection means for measuring the electron temperature of said plasma, said electron temperature being determined, for a first light source having a predetermined brightness temperature and wavelength, from the first and second output signals of said detection means;
  second separation means for separating the light in said second portion into two components;
  second detection means for detecting the two light components in said second light portion;
  analyzer means interposed between said second separation means and said second detection means for measuring the Faraday angle of said plasma; and
  second processing means coupled to said second detection means for measuring the electron density and conductivity of said plasma, said electron density and conductivity being determined, for plasma electrons having a predetermined characteristic frequency, from the Faraday rotation angle of said plasma as measured by said analyzer means.

6. A device for measuring plasma properties as set forth in claim 5, wherein said first light source projects light having a wavelength in the ultraviolet range, and said second light source projects light having a wavelength in the far infrared range.

7. Apparatus for optically measuring the electron temperature, electron density and conductivity of a plasma as set forth in claim 5, wherein the electron temperature of said plasma is determined by solving in said first processing means the equation $$Te = T_L \left\{ 1 - \frac{\lambda \cdot T_L}{C_2} \ln \left[ \frac{\xi \cdot K_1 \cdot \phi_P}{\phi_{LS} - \phi_S + \phi_P} \right] \right\}^{-1}$$

where, Te is the plasma electron temperature, $T_L$ the brightness temperature of the light source, $\lambda$ the wavelength of the light generated by the light source, $C_2$ a correction factor, $\xi$ the transmission coefficient of a polarizer for linearly polarizing the light, $K_1$ a correction factor for an optical system between the light source and the plasma, $\phi_p$ the output from the detection means for detecting the P-polarized component, $\phi_{LS}$ the intensity of the light flux after passing through the plasma, and $\phi_S$ the output from the detection means for detecting the S-polarized component; and
  wherein the conductivity and electron density of said plasma are determined by solving in said second processing means the equations $$N = \frac{\theta(\omega_0^2 - \omega^2)^2}{a\omega^2} \text{ and}$$

-continued $$\sigma = Ne\mu, \text{ respectively,}$$

where N is the electron density of the plasma, $\theta$ the Faraday rotation angle of said plasma measured by said analyzer, $\omega_0$ the characteristic frequency of the plasma electrons, $\omega$ the frequency of the incident light, e a quantum of electricity, $\mu$ the mobility of electrons in the plasma and $$a = \frac{e^3 B d}{2m^2 nc}, \text{ where}$$

B is the magnetic field intensity of the plasma, d the thickness of the plasma, m the mass of an electron, n the refractive index of the plasma, and c the velocity of light.

8. Apparatus for measuring plasma properties as set forth in claim 5 wherein the wavelength of the light generated by said second light source is longer than the wavelength of the light generated by said first light source, the light generated by said second light source being affected to a greater extent by the Faraday effect than the light generated by said first light source.

9. A device for measuring plasma properties as set forth in claim 5, wherein said first light source projects light having a wavelength in the visible range, and said second light source projects light having a wavelength in the far infrared range.

10. The method of optically measuring the temperature of a plasma comprising the steps of
  generating linearly polarized light, said linearly polarized light being incident on said plasma;
  separating light emanating from siad plasma into an S-polarized component and a P-polarized component;
  detecting said S-polarized and P-polarized components, and generating first and second signals corresponding to said S-polarized and P-polarized components respectively, and
  processing said first and second signals to measure the electron temperature of said plasma, said electron temperature being determined, for a light source having a predetermined brightness temperature and wavelength, from said first and second signals.

11. The method of optically measuring the temperature of a plasma as set forth in claim 10, wherein the electrons temperature of said plasma is determined by solving in said processing means the equation $$Te = T_L \left\{ 1 - \frac{\lambda \cdot T_L}{C_2} \ln \left[ \frac{\xi \cdot K_1 \cdot \phi_P}{\phi_{LS} - \phi_S + \phi_P} \right] \right\}^{-1}$$

where, Te is the plasma electron temperature, $T_L$ the brightness temperature of the light source, $\lambda$ the wavelength of the light generated by the light source, $C_2$ a correction factor, $\xi$ the transmission coefficient of a polarizer for linearly polarizing the light, $K_1$ a correction factor for an optical system between the light source and the plasma, $\phi_p$ the output from the detection means for detecting the P-polarized component, $\phi_{LS}$ the intensity of the light flux after passing through the plasma, and $\phi_S$ the output from the detection means for detecting the S-polarized component.

12. The method of optically measuring the electron temperature, electron density and conductivity of a plasma, comprising the steps of
  generating a first linearly polarized light component having a first wavelength;
  generating a second linearly polarized light component having a second wavelength different from said first wavelength, said first and second linearly polarized light components being incident on said plasma along a common optical axis;
  dividing light emanating from said plasma in response to said first and second light components into first and second portions;
  separating the light in said first portion into an S-polarized component and a P-polarized component;
  detecting said S-polarized and P-polarized components in said first portion, and generating first and second signals corresponding to said S-polarized and P-polarized components respectively;
  processing said first and second signals to measure the electron temperature of said plasma, said electron temperature being determined, for a light source having a predetermined brightness temperature and wavelength, from said first and second signals;
  separating the light in said second portion into two components;
  detecting the two light components in said second light portion;
  measuring by means of the two light components in said second light portion the Faraday angle of said plasma; and
  processing the two light components in said second light portion to measure the electron density and conductivity of said plasma, said electron density and conductivity being determined, for plasma electrons having a predetermined characteristic frequency, from the Faraday rotation angle of said plasma.

13. The method of optically measuring the electron temperature, electron density and conductivity of a plasma as set forth in claim 12, wherein the electron temperature of said plasma is determined by solving in said first processing means the equation $$Te = T_L \left\{ 1 - \frac{\lambda \cdot T_L}{C_2} \ln \left[ \frac{\xi \cdot K_1 \cdot \phi_P}{\phi_{LS} - \phi_S + \phi_P} \right] \right\}^{-1}$$

where, Te is the plasma electron temperature, $T_L$ the brightness temperature of the light source, $\lambda$ the wavelength of the light generated by the light source, $C_2$ a correction factor, $\xi$ the transmission coefficient of a polarizer for linearly polarizing the light, $K_1$ a correction factor for an optical system between the light source and the plasma, $\phi_p$ the output from the detection means for detecting the P-polarized component, $\phi_{LS}$ the intensity of the light flux after passing through the plasma, and $\phi_S$ the output from the detection means for detecting the S-polarized component; and
  wherein the conductivity and electron density of said plasma are determined by solving in said second processing means the equations $$N = \frac{\theta(\omega_0^2 - \omega^2)^2}{a\omega^2} \text{ and}$$

-continued $\sigma = Ne\mu$, respectively, where N is the electron density of the plasma, $\theta$ the Faraday rotation angle of said plasma measured by said analyzer, $\omega_0$ the characteristic frequency of the plasma electrons, $\omega$ the frequency of the incident light, e a quantum of electricity, $\mu$ the mobility of electrons in the plasma and $$a = \frac{e^3 Bd}{2m^2 nc}, \text{ where}$$

B is the magnetic field intensity of the plasma, d the thickness of the plasma, m the mass of an electron, n the refractive index of the plasma, and c the velocity of light.

14. The method of optically measuring the electron density and conductivity of a plasma, comprising the steps of
generating linearly polarized light, said light being incident on said plasma;
separating light emanating from said plasma into two components;
detecting said two light components;
measuring by means of said two light components the Faraday angle of said plasma; and
processing said two light components to measure the electron density and conductivity of said plasma, said electrons having a predetermined characteristic frequency, from the Faraday rotation angle of said plasma.

15. The method of optically measuring the electron density and conductivity of a plasma as set forth in claim 14, wherein the conductivity and electron density of said plasma are determined by solving in said processing means the equations $$N = \frac{\theta(\omega_0^2 - \omega^2)^2}{a\omega^2} \text{ and}$$

$\sigma = Ne\mu$, respectively, where N is the electron density of the plasma, $\theta$ the Faraday rotation angle of said plasma measured by said analyzer, $\omega_0$ the characteristic frequency of the plasma electrons, $\omega$ the frequency of the incident light, e a quantum of electricity, $\mu$ the mobility of electrons in the plasma and $$a = \frac{e^3 Bd}{2m^2 nc}, \text{ where}$$

B is the magnetic field intensity of the plasma, d the thickness of the plasma, m the mass of an electron, n the refractive index of the plasma, and c the velocity of light.

* * * * *